United States Patent [19]
Johnson

[11] Patent Number: 6,125,705
[45] Date of Patent: Oct. 3, 2000

[54] APPARATUS FOR THE CONCURRENT ULTRASONIC INSPECTION OF PARTIALLY COMPLETED WELDS

[75] Inventor: John A. Johnson, Idaho Falls, Id.

[73] Assignee: Bechtel BWXT Idaho, LLC, Idaho Falls, Id.

[21] Appl. No.: 09/066,723

[22] Filed: Apr. 23, 1998

[51] Int. Cl.[7] .................................................. G01N 29/00
[52] U.S. Cl. .................................................. 73/622; 73/598
[58] Field of Search ........................... 73/620, 579, 598, 73/618, 622, 637, 638, 640

[56] References Cited

U.S. PATENT DOCUMENTS

| | | | |
|---|---|---|---|
| 3,575,042 | 4/1971 | Lovelace et al. | 73/613 |
| 4,173,898 | 11/1979 | Forstermann et al. | 73/611 |
| 4,285,243 | 8/1981 | Collingwood | 73/623 |
| 4,351,190 | 9/1982 | Rehme et al. | 73/638 |
| 4,375,165 | 3/1983 | de Sterke | 73/622 |
| 4,395,911 | 8/1983 | Macecek | 73/622 |
| 4,555,948 | 12/1985 | Miyamoto et al. | 73/640 |
| 4,627,289 | 12/1986 | Fukuda et al. | 73/622 |
| 5,060,518 | 10/1991 | Aleshin et al. | 73/620 |
| 5,108,693 | 4/1992 | Landry et al. | 376/245 |
| 5,439,157 | 8/1995 | Geier et al. | 228/9 |
| 5,537,876 | 7/1996 | Davidson et al. | 73/624 |
| 5,583,292 | 12/1996 | Karbach et al. | 73/638 |
| 5,619,423 | 4/1997 | Scrantz | 364/507 |

*Primary Examiner*—Max Noori
*Attorney, Agent, or Firm*—Wells St John Roberts Gregory & Matkin

[57] ABSTRACT

An apparatus for the concurrent nondestructive evaluation of partially completed welds is described and which is used in combination with an automated welder and which includes an ultrasonic signal generator mounted on the welder and which generates an ultrasonic signal which is directed toward one side of the partially completed welds; an ultrasonic signal receiver mounted on the automated welder for detecting ultrasonic signals which are transmitted by the ultrasonic signal generator and which are reflected or diffracted from one side of the partially completed weld or which passes through a given region of the partially completed weld; and an analysis assembly coupled with the ultrasonic signal receiver and which processes the ultrasonic signals received by the ultrasonic signal receiver to identify welding flaws in the partially completed weld.

41 Claims, 9 Drawing Sheets

APPARATUS FOR THE CONCURRENT ULTRASONIC INSPECTION OF PARTIALLY COMPLETED WELDS

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

TECHNICAL FIELD

The present invention relates to an apparatus which facilitates the concurrent nondestructive evaluation of partially completed welds.

BACKGROUND OF THE INVENTION

Thick sectional welds are usually made in several passes. In this regard, it should be understood that the area between two adjacent parts to be joined is filled up a portion at a time. In the testing of such thick sectional welds, ultrasonic sensors and other nondestructive evaluation methods are often used to inspect same. However, under most circumstances, this inspection is almost always done a long time after the welding process has been completed and the weld has cooled down. It has long been known that when welding defects are detected on a pass-by-pass basis, they can be easily repaired before being covered by the welding material laid down by subsequent welding passes. Thus, for example, a defect in the root pass can be repaired easily and economically without grinding out all of the welding metal from the later passes. This welding method contrasts with inspecting a completed weld, because a significant amount of weld metal may have to be subsequently removed to reach the welding defect. Still further, and as discussed in U.S. Pat. No. 4,712,722, a significant economic and productivity advantage can be obtained if welding flaws can be substantially, concurrently detected and repaired on a pass-by-pass basis.

In U.S. Pat. No. 4,712,722, the teachings of which are incorporated by reference herein, several forms of a method and device which implements a pass-by-pass inspection of partially completed welds are described. While the apparatus and method described in that patent has worked with some degree of success, several shortcomings have been identified which have detracted from its usefulness. For example, it has been discovered that the method and apparatus as described in the earlier U.S. Pat. No. 4,712,722, is not completely satisfactory for inspection of all weld geometries.

Still further, the method and apparatus as described in U.S. Pat. No. 4,712,722, does not locate with any degree of precision, the precise location of the weld defect. Yet still further, the method and apparatus as described in U.S. Pat. No. 4,712,722, does not appear to provide a convenient means for verifying the presence of a welding defect.

In view of the foregoing, it would be highly desirable to provide a method and apparatus which can address these perceived and other shortcomings in a novel device and method which facilitates the concurrent nondestructive evaluation of partially completed welds.

SUMMARY OF THE INVENTION

In its broadest aspect, the present invention relates to an apparatus for the concurrent nondestructive evaluation of partially completed welds which have opposite sides and which is used in combination with an automated welder; and wherein the apparatus includes an ultrasonic signal generator mounted on the welder and which generates an ultrasonic signal which is directed towards one side of the partially completed weld; an ultrasonic signal receiver mounted on the welder for detecting ultrasonic signals which are transmitted by the ultrasonic signal generator and which are reflected or diffracted from one side of the partially completed weld, or which passes through a given region of the partially completed weld; and an analysis assembly coupled with the ultrasonic signal receiver and which processes the ultrasonic signals received by the ultrasonic signal receiver to identify welding flaws in the partially completed weld.

BRIEF DESCRIPTION OF THE DRAWINGS

Preferred embodiments of the invention are described below with reference to the following accompanying drawings which are briefly described in the paragraphs which follow.

DETAILED DESCRIPTION OF THE PREFERRED EMBODIMENTS

Figure 1:
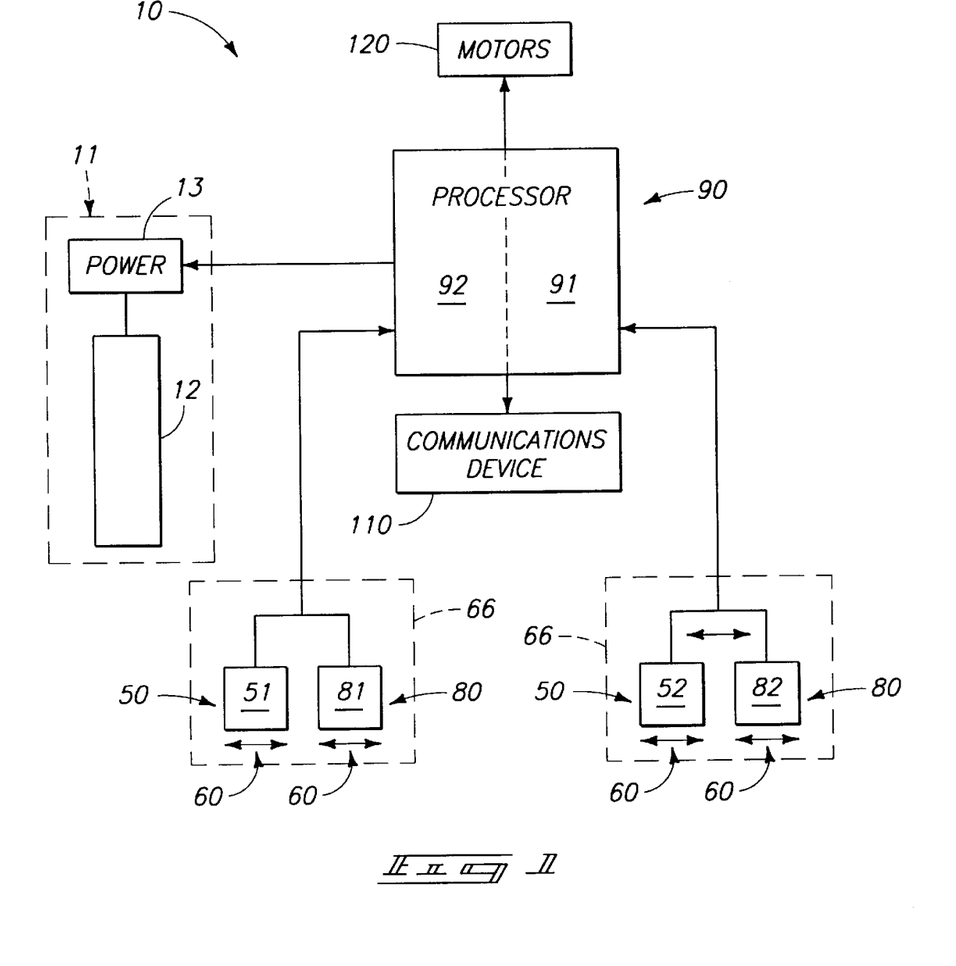
FIG. 1 is a greatly simplified schematic diagram of the present invention.
Figure 7:
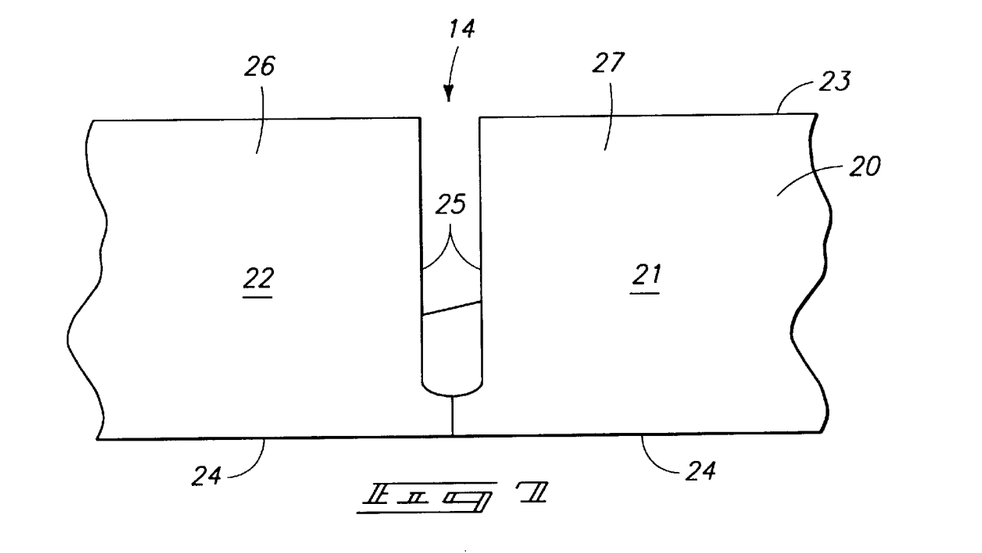
FIG. 7 is a transverse, vertical sectional view taken through two objects to be joined and which shows the geometry of a typical weld.
Figure 8:
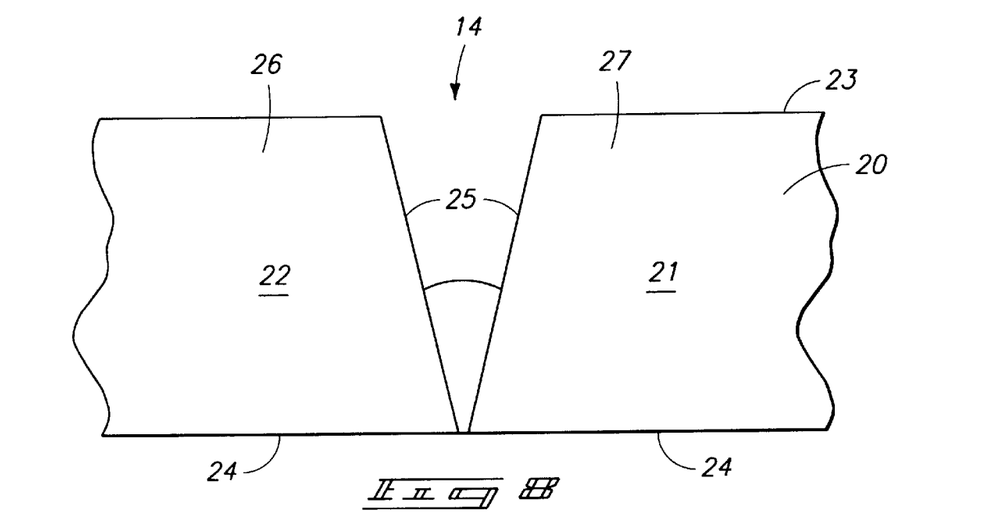
FIG. 8 is a transverse, vertical sectional view taken through two objects to be joined and which shows a weld having a second type of geometry.

The apparatus for the concurrent nondestructive evaluation of partially completed welds is best understood by a study of FIG. 1. As shown therein, the apparatus 10 is shown in a very simplified schematic diagram. In FIG. 1, the apparatus 10 includes an automated movable welder which is schematically indicated by the numeral 11. Automated movable welders are familiar to those who are skilled in the art, and therefore, a detailed discussion of these devices is neither warranted nor necessary for an understanding of the invention. However, it should be appreciated that the automated movable welder is operable to be attached to a given object which is to be welded. The automated welder then moves repeatedly along a prescribed path of travel to achieve a given welding objective. As seen in FIG. 1, the automated movable welder includes a welding head 12 which has a power supply 13 connected thereto. The power supply 13 supplies the electricity necessary to perform the welding activity. As seen most clearly by reference to FIG. 2, the welding head 12 is shown in a given position to achieve a desired welding objective with respect to a partially completed weld which is shown generally by the numeral 14. The welding head 12 is movable along a given path of travel which is generally indicated by the numeral 15. The automated movable welder 11 is operable to weld a given substrate designated by the numeral 20. The substrate comprises first and second sections 21 and 22, respectively, which are positioned in juxtaposed relation, one to the other. FIGS. 7 and 8 show two given weld geometries, however, other geometries are possible. Each of the sections 21 and 22 to be welded, includes a top surface 23, a bottom surface 24, and a sidewall 25. The partially completed weld 14 has opposite sides 26 and 27 respectively.

Figure 2:
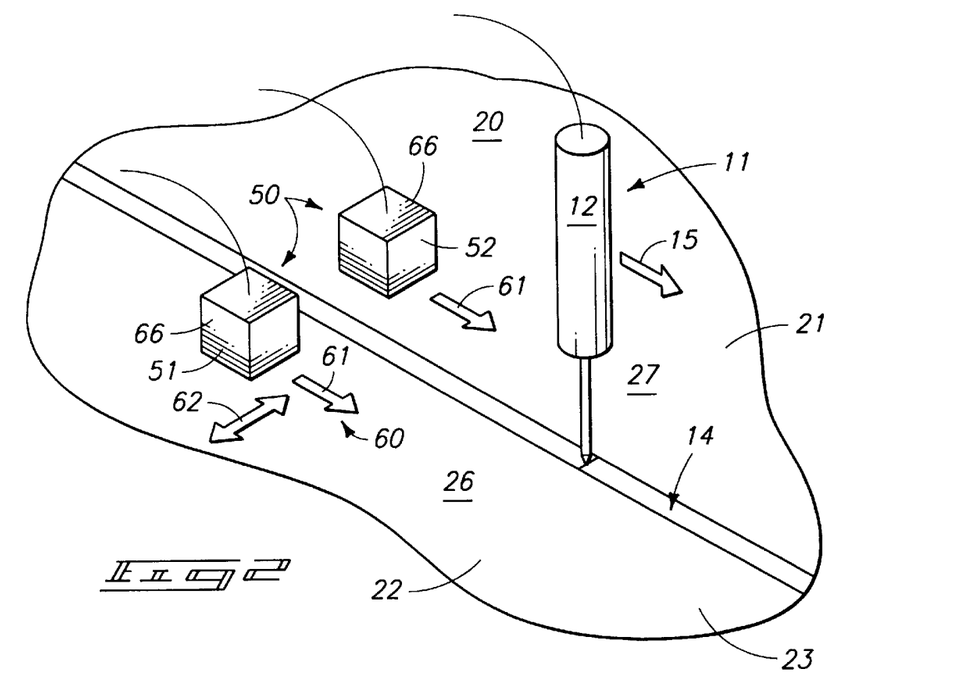
FIG. 2 is a greatly simplified view of a first form of the present invention with supporting surfaces removed to show the structure thereunder.
Figure 3:
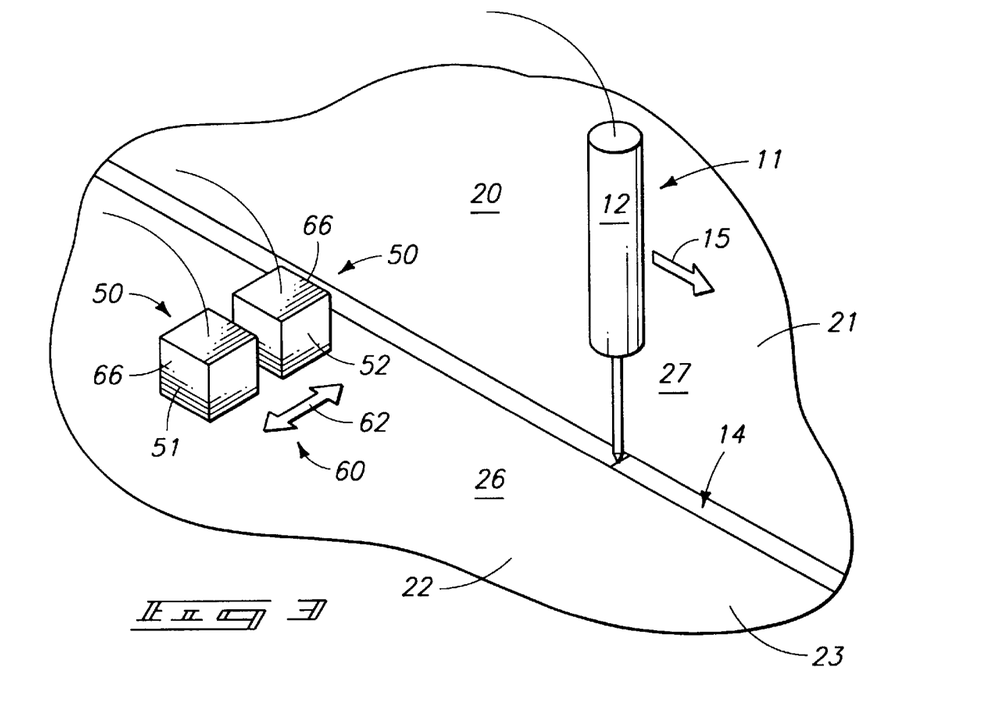
FIG. 3 is a greatly simplified view of a second form of the present invention with supporting surfaces removed to show the structure thereunder.
Figure 4:
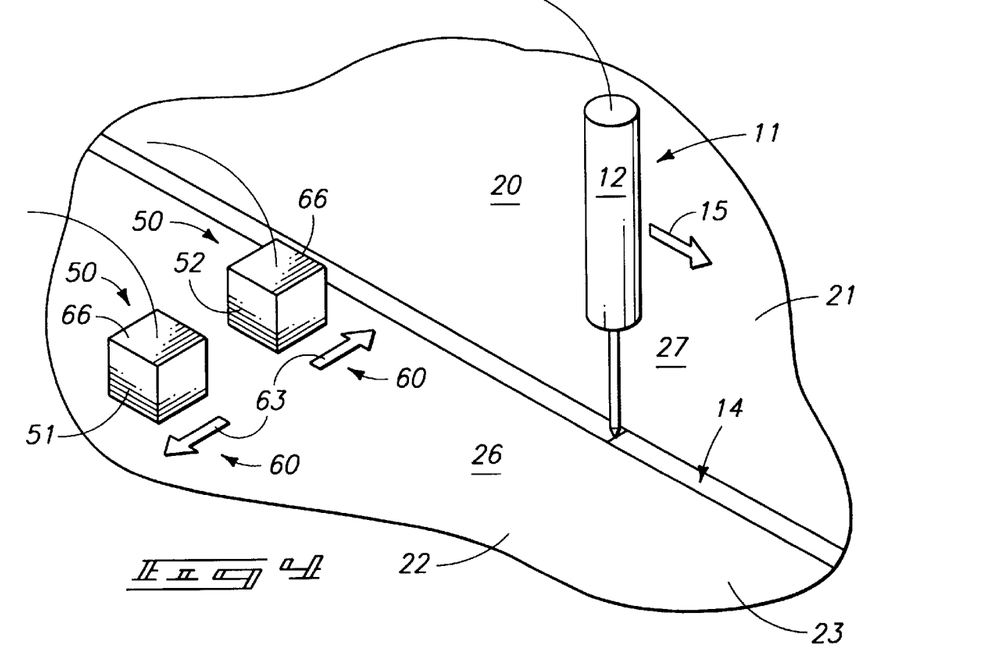
FIG. 4 is a greatly simplified view of a third form of the present invention with supporting surfaces removed to show the structure thereunder.
Figure 5:
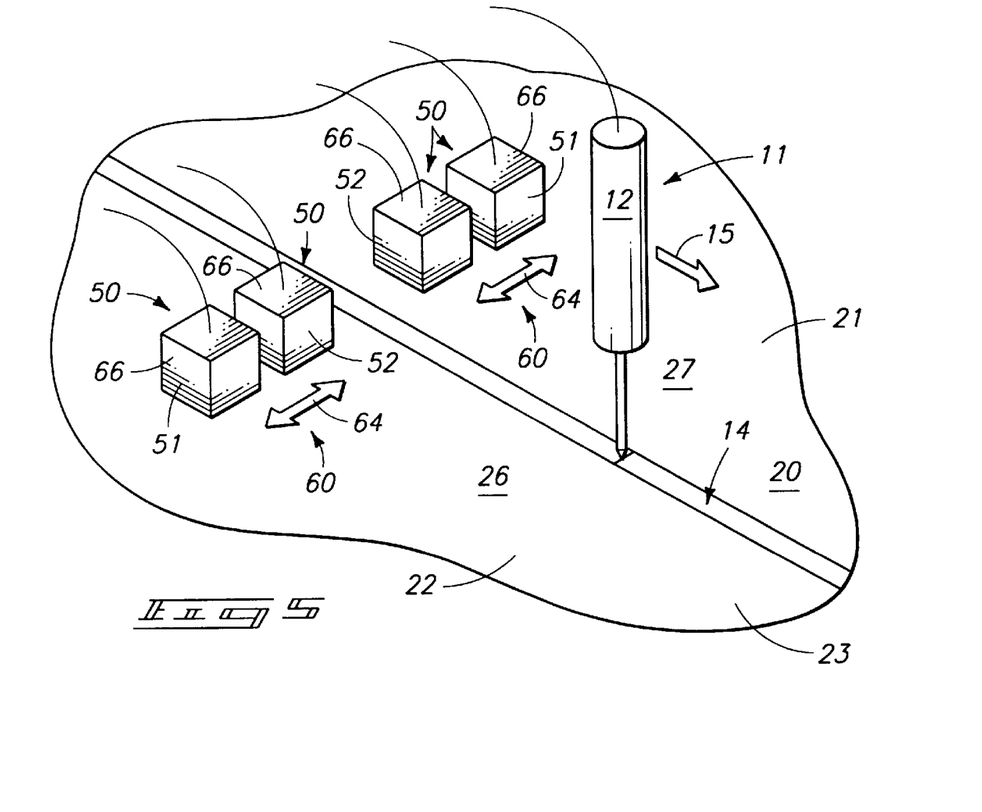
FIG. 5 is a greatly simplified view of a fourth form of the present invention with supporting surfaces removed to show the structure thereunder.
Figure 6:
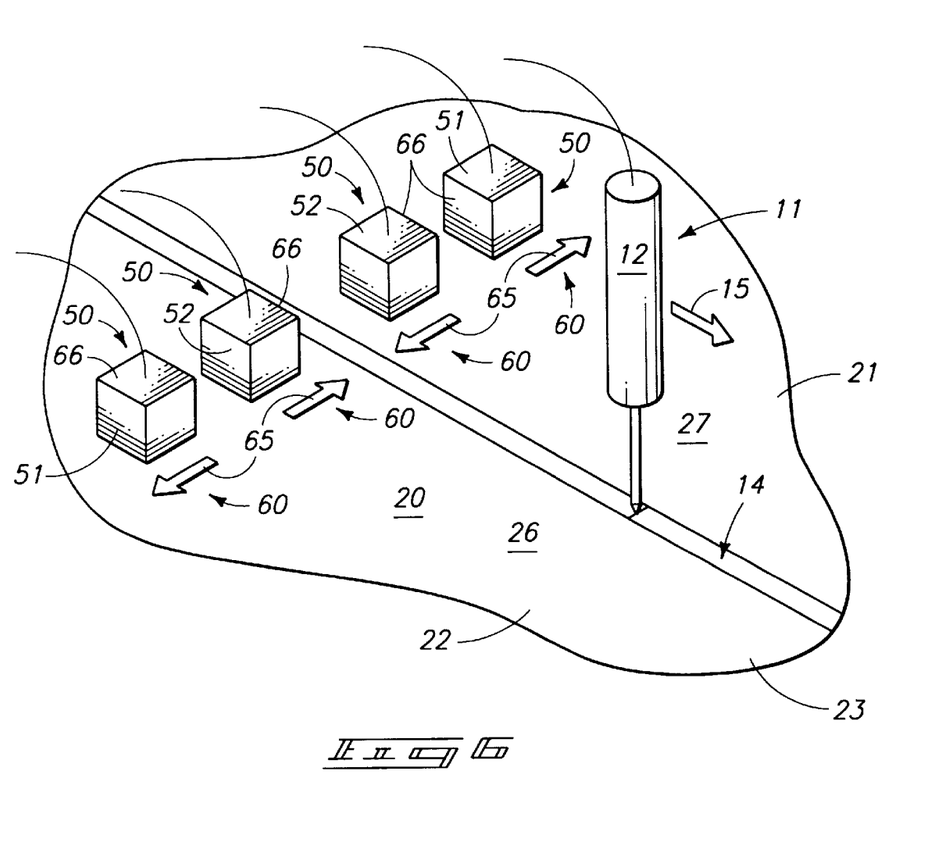
FIG. 6 is a greatly simplified view of a fifth form of the present invention with supporting surfaces removed to show the structure thereunder.

As seen most clearly in FIGS. 1 through 6, the apparatus 10 of the present invention includes an ultrasonic signal generator 50 which is mounted on the automated movable welder 11, and which generates an ultrasonic signal which is directed towards one side of the partially completed weld 14. The ultrasonic signal generator is mounted in spaced trailing relation relative to the path of movement of automated welder 11. As seen in FIG. 2 through 6, the ultrasonic signal generator may include first and second ultrasonic signal generators 51 and 52 which are mounted, in one form of the invention, on the opposite sides 26 and 27 of the partially completed weld 14 (FIG. 2). In this form of the invention, the ultrasonic signal generators 51 and 52 are movable along a plurality of paths of travel designated by the numeral 60. These paths of travel have various components. For example, the paths of travel 60 may include a first component 61 which is generally oriented in substantially parallel, spaced relation with the path of travel of the automated welder 11. The path of travel 60 may include a second component 62 which is substantially laterally outwardly relative to the particular completed weld 14. As seen in FIG. 3, there is illustrated a second form of the invention whereby the first and second ultrasonic signal generators 51 and 52, move substantially in unison, substantially laterally outwardly relative to the orientation of the partially completed weld 14. As seen, the signal generators are on the same side of the partially completed weld 14. As seen in FIG. 4, there is shown a third form of the invention whereby first and second ultrasonic signal generators 51 and 52, may have individual paths of travel which are substantially coaxially aligned, but which are additionally independently movable and in a direction which is laterally outwardly relative to the orientation of the partially completed weld 14. Still further, and as seen in the fourth form of the invention in FIG. 5, the first and second ultrasonic signal generators 51 and 52 may be coupled in discrete pairs on the opposite sides 26 and 27 of the partially completed weld 14. In this arrangement, the pairs of ultrasonic signal generators 51 and 52 move in unison substantially laterally outwardly and transversely relative to the direction of the partially completed weld 14. Finally, in the fifth form of the invention, as seen in FIG. 6, the ultrasonic signal generators 51 and 52 may move independently of each other, and substantially laterally outwardly and substantially transversely relative to the orientation of the partially completed weld 14.

In the present invention, as shown in FIGS. 1 through 6, it should be understood that the apparatus 10 may be implemented by utilizing discrete ultrasonic signal generators 50 or in the alternative, by utilizing a transducer 66 which performs both the function of an ultrasonic signal generator 50, and an ultrasonic signal receiver, as will be described hereinafter.

Figure 9:
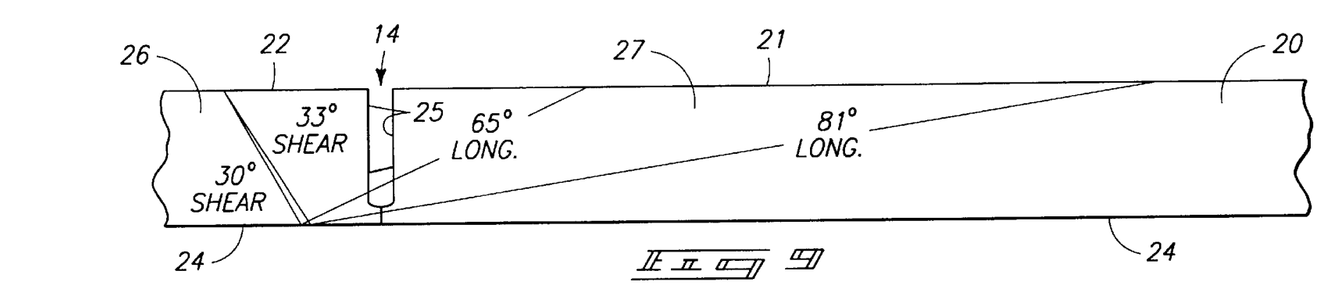
FIG. 9 is a transverse, vertical sectional view taken through two welded objects and which shows various ultrasonic signal paths.
Figure 15:
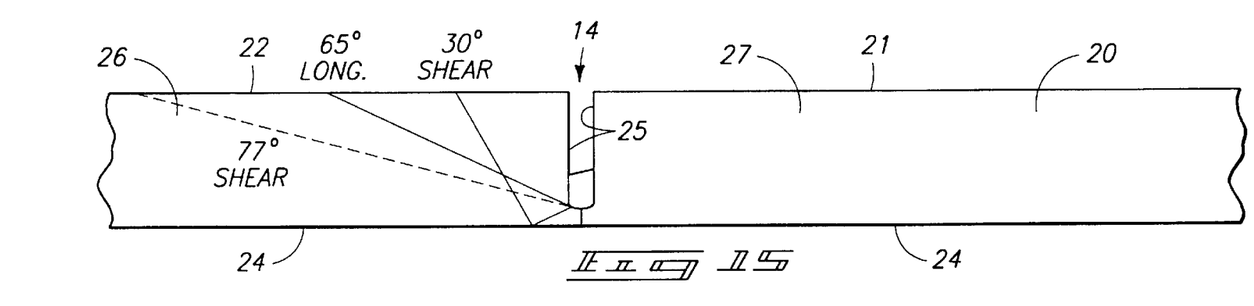
FIGS. 15, 16 and 17 show another given weld geometry and the ultrasonic signal paths which are utilized to analyze that weld geometry.

As best seen in FIG. 1, the apparatus for the concurrent nondestructive evaluation of partially completed welds 10 includes an ultrasonic signal receiver which is designated generally by the numeral 80. As seen in FIGS. 2 through 6, the ultrasonic receiver may be incorporated into the structure of a conventional transducer 66 as earlier described, or may comprise individual first and second ultrasonic signal receivers 81 and 82 respectively. As is described, above, with respect to the paths of travel 60 of the ultrasonic signal generator 50, it should be appreciated that the ultrasonic signal receiver 80 moves along substantially the same courses of travel in the combinations as earlier described. As seen in FIG. 1, the ultrasonic signal receiver 80 is mounted on the automated movable welder 11 and detects ultrasonic signals which are transmitted by the ultrasonic signal generator 50 and which are reflected or diffracted from one side of the partially completed weld 14 or which passes through a given region of the partially completed weld 14. Such is seen in FIGS. 9 and 15, for example.

As seen in FIG. 1, an automated signal processor 90 is provided and which couples the ultrasonic signal generator and receiver together. The signal processor 90 includes an analysis assembly 91 which is coupled with the ultrasonic signal receiver 80 and which processes the ultrasonic signals received by the ultrasonic signal receiver to identify predetermined welding flaws in the partially completed weld 14.

Still further, the processor 90 includes a control assembly 92 which is coupled with the automated welder 11, and the analysis assembly 91, and which stops the operation of the automated movable welder 11 when the number of welding flaws reach a predetermined number or given size. Additionally, the control assembly may, in some forms of the invention, control the generation of the ultrasonic signals. In operation, and as best appreciated by a study of FIGS. 2, through 17, the analysis assembly 91 receives several ultrasonic signals from the respective ultrasonic signal receiver 80. These signals are subsequently correlated by the analysis assembly to confirm the presence, location and type of a given welding flaw. This aspect of the present invention will be discussed in greater detail, hereinafter.

A communications device 110 (FIG. 1) is coupled with the analysis assembly 91 and identifies the location of each welding flaw which exceeds predetermined parameters. The communications device 110 can comprise a number of different assemblies, but as a general matter the communications device provides machine readable indicia which identifies the type and location of the welding flaw such that an operator can then perform corrective action to remedy the given welding flaw before the automated welder makes a subsequent pass through the same physical location. Still further, and as seen in FIG. 1, the analysis assembly 91 is coupled with at least one motor 120 which controls the position of the ultrasonic signal generator 50 or signal receiver 80 along the respective paths of travel earlier described to achieve the benefits which will be discussed, below. It should be understood that the motor 120 provides a means by which the respective ultrasonic signal generators and receivers 50 and 80 can be adjusted during on-going welding operations.

In this regard, and as further background to the present invention, it is well known that when an ultrasonic wave travels in a solid medium and impinges on a plane surface, two reflected waves can be produced. One wave is reflected at the same angle as the incident wave and has the same mode (either longitudinal or shear), and the other wave, which has been termed the mode converted wave, is of the other mode and reflects at a different angle. For example, an incident shear wave is divided into a reflected shear wave and a reflected longitudinal wave. In addition, two wave modes may also be transmitted into the medium onto the other side of the plane. The two wave modes travel at different speeds and these determine the angle of reflection of the mode converted wave. The following formula relates to these phenomena.

$$\frac{\text{SIN}(\theta_{shear})}{V_{shear}} = \frac{\text{SIN}(\theta_{longitudinal})}{V_{longitudinal}}$$

In this formula, V is the shear or longitudinal wave velocity. In the example noted above, the velocities are taken to be those of typical carbon steel, that is, 3.2 millimeters per microsecond for the shear wave, and 5.8 millimeters per microsecond for the longitudinal wave. In the present invention 10, it has been determined that if the incident wave is a shear wave, and the incident wave is beyond a given angle called the critical angle, then no longitudinal waves are produced. In this regard, the critical angle has been determined to be where the longitudinal wave angle is 90° and sine of the longitudinal angle is 1. For incident shear angles greater than this critical angle, the formula, noted above, predicts that the sine of the longitudinal wave is greater than 1.

Figure 10:
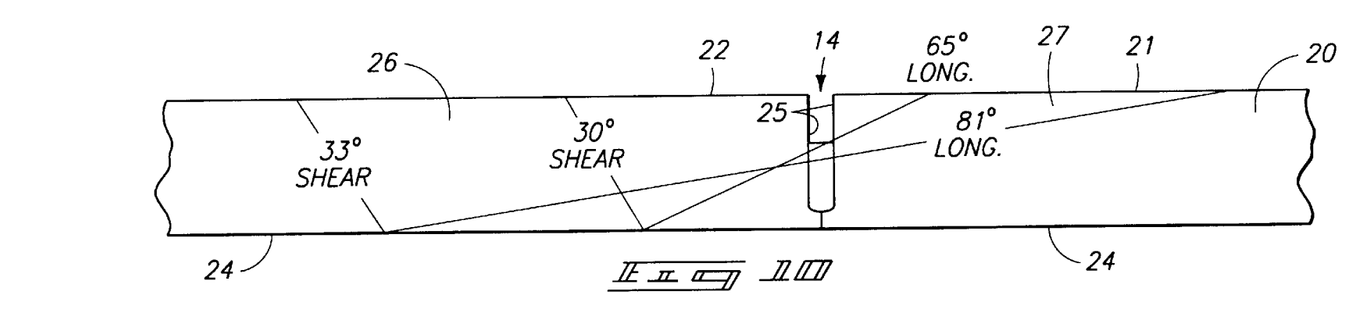
FIG. 10 is a transverse, vertical sectional view taken through two welded objects and which shows the paths of various ultrasonic signals.
Figure 11:
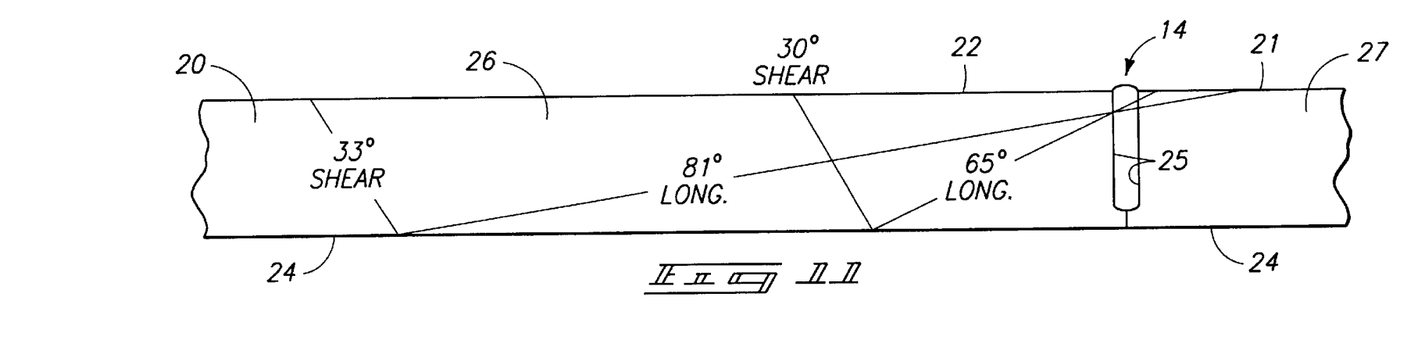
FIG. 11 is a transverse, vertical sectional view taken through two welded objects and which shows the paths of various ultrasonic signals.

As best seen by reference to FIGS. 7 and 8, two geometries of partially completed welds 14 are shown. One of the perceived shortcomings of the prior art has been the identification and confirmation of the welding flaws present in partially completed welds 14 of different geometries. FIGS. 9, 10 and 11 show possible ultrasonic beam positions and angles for inspecting partially completed narrow groove welds such as seen in FIG. 7, by utilizing the apparatus 10 of the present invention. In FIGS. 9, 10 and 11, the movement of the respective ultrasonic signal generators 50 and ultrasonic signal receivers 80 to discrete positions substantially laterally outwardly relative to the partially completed weld 14 permits the present invention to detect such defects as lack of sidewall fusion (LOF defects) in a partially completed narrow-groove weld. The technique of transmitting and receiving ultrasonic signals as shown in FIGS. 9, 10 and 11 has been termed "pitch-catch ultrasonics". This technique uses mode conversion of the ultrasonic wave. In the drawings as shown, all the angles illustrated are with respect to a line perpendicular to the surface of the part which is being welded. The specific values of the angles are typical values. In each of the figures which are described below, a transducer 66 is provided which transmits or receives ultrasonic signals at the top surface 23 of the first and second sections 21 and 22 respectively. For example, and referring now to FIG. 9, a transducer 66 which is located on the second section 22 generates a 30° shear wave. This wave mode-converts off the bottom surface 24 of the second section 22 to a 65° longitudinal wave. If a LOF defect exists in the path of the ultrasonic beam the amplitude of the ultrasonic beam received by the transducer 66 which is located at the position of the intersection of the top surface 23, of the first section 21, will be significantly reduced as compared to the amplitude received without the presence of an LOF defect. Therefore, the loss of amplitude at the receiver transducer is indicative of the presence of an LOF defect.

This relationship, of course, is reciprocal, that is, a transducer 66 which is positioned on the first section 21 and which generates a 65° longitudinal wave will mode convert to a shear wave after passing through the partially completed weld 14. This can be received by the transducer 66 which is located on the second section 22 at the position of the intersection of the top surface 23 and the 30° shear wave beam. Again, a loss of amplitude at the receiving transducer 66 is indicative of the presence of an LOF in the beam path. Also shown in FIGS. 8 and 9 is a 33° shear wave and its mode converted 81° longitudinal wave, or the reverse thereof. These other angles can be used to inspect different regions of the weld as seen in the drawing. In addition, the beam spread of the transducer 66 can be set to inspect large areas of the weld all at once. As will be recognized by a study of FIGS. 1, 9 and 10, the motor 120 would be utilized to move the respective ultrasonic signal generators 50 and ultrasonic signal receiver 80 to given predetermined locations laterally outwardly relative to the partially completed weld 14 to achieve the aforementioned objectives. As will be recognized, FIGS. 9, 10 and 11 illustrate the transmission and receiving of the ultrasonic signals by transducers 66 which are positioned on the opposite sides 26 and 27 of the partially completed weld 14. It is possible, of course, to have individual pairs of transducers. For example, in FIGS. 5 and 6, ultrasonic waves can be generated and received from either side of the partially completed weld, and the correlation of the received signals, by the analysis assembly 91, provides a conformation of the presence of a welding defect as well as precisely identifying the location of the weld defect.

The aforementioned example relates to a pitch-catch method where mode conversion takes place. This same invention may be utilized in those situations when mode conversion does not take place. In this method, which can also be used to detect LOF welding defects, the ultrasonic signals' angle of reflection off the surface 24 is equal to the angle of incidence. Any convenient angle can be utilized. In this method, the transducer 66 generates an angled beam that reflects off the surface 24 and travels through the partially completed weld 14. If an LOF welding defect exists in the path of the ultrasonic signal the amplitude of the received signal at the surface 23 will be significantly reduced as compared to a received signal without the presence of an LOF welding defect. Either longitudinal or shear modes may be used in this variation. However, shear beams beyond the critical angle appear to be preferred because no mode converted waves appear to be generated which would interfere with the measurement of the ultrasonic signal.

Figure 12:
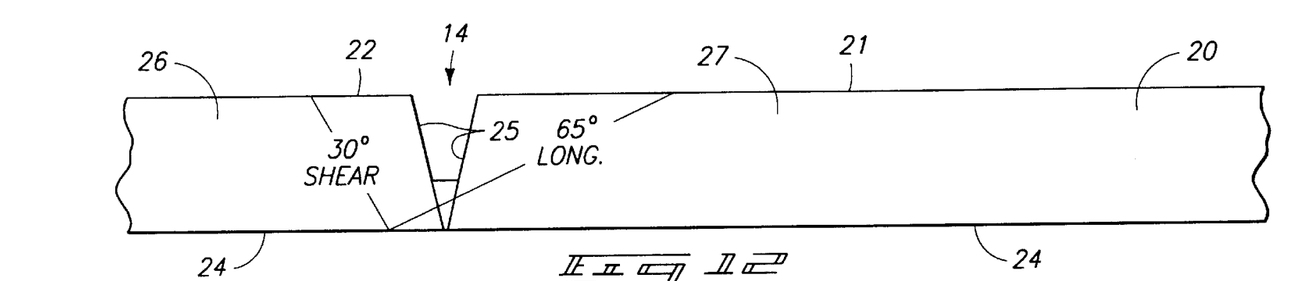
FIGS. 12, 13 and 14 shows a weld having a given geometry and the paths of typical ultrasonic signals which are utilized to analyze that weld geometry.
Figure 13:
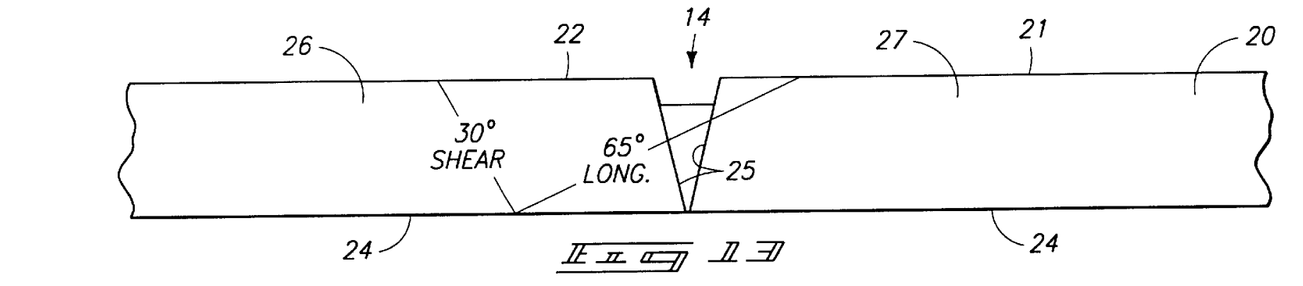
Figure 14:
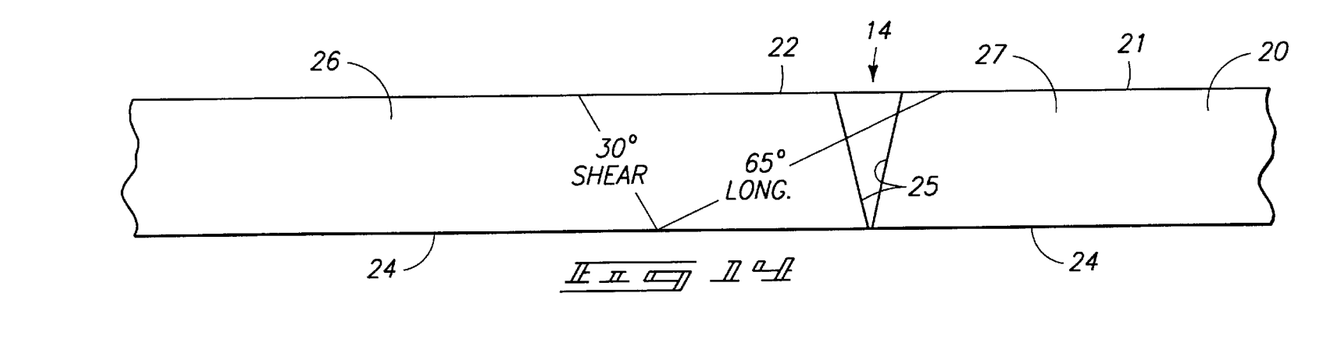

In FIGS. 12, 13 and 14, a similar situation is presented for a partially completed weld which has a V shaped geometry.

Here, the same shear and longitudinal wave combinations are used to detect a weld defect in various regions of the partially completed weld through which the ultrasonic beam passes. As was the case with the narrow groove weld geometry, a small variation in the shear angle can be used to inspect different regions of the sidewall 25. As will be recognized, the ultrasonic signal generator and receiver 50 and 80 are moved generally laterally outwardly relative to the partially completed weld 14 to appropriate locations so that they can receive or generate the appropriate ultrasonic signals.

Figure 16:
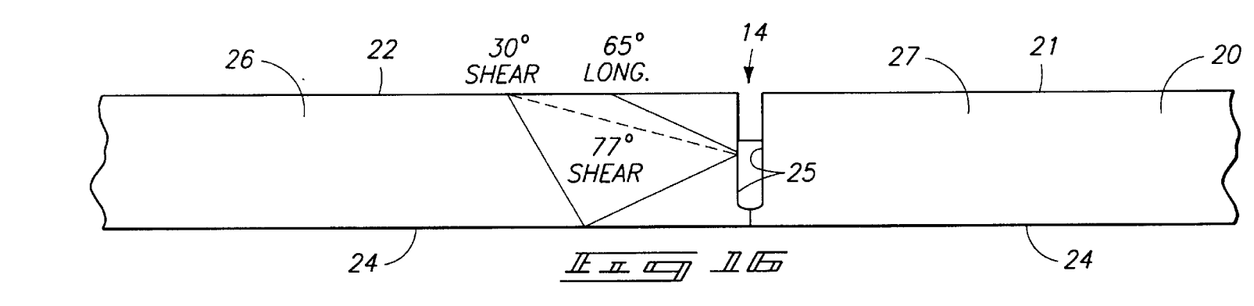
Figure 17:
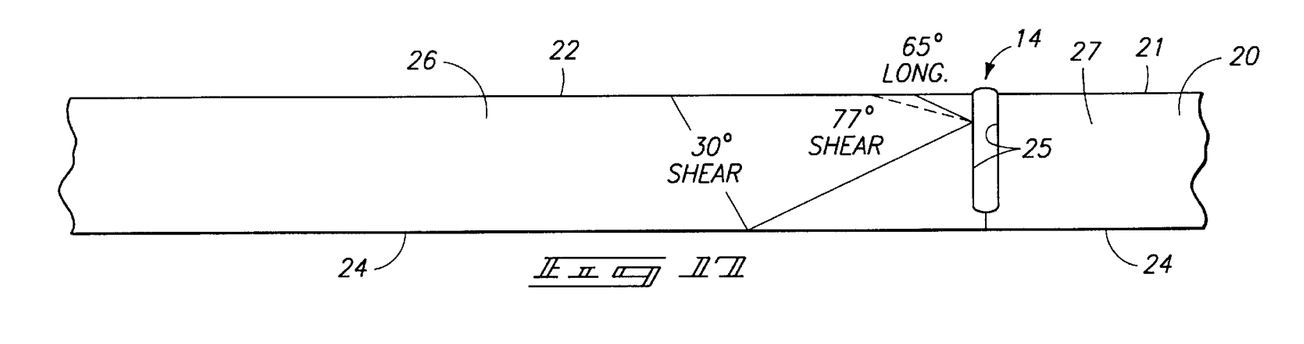

Referring now to FIGS. 15, 16, and 17, LOF welding flaws will also cause some ultrasonic energy to be reflected. A reflection from an LOF welding flaw is dependent on the orientation of same. Under most circumstances, the defects are generally parallel to the sidewall 25. The LOF welding defect acts in some manner like a plane reflector. As seen in FIGS. 15, 16, and 17, the reflected energy from an LOF welding defect gives rise to several additional uses of the present apparatus 10 and method. For example, and as seen in FIG. 15, a transducer 66 produces a 30° shear wave that mode converts off of the bottom surface 24 to a 65° longitudinal wave. This longitudinal wave will reflect off an LOF in the partially completed weld 14. This reflection can be received by a transducer 66. The transducer produces a signal indicating the detection of the defect. As earlier discussed, the present apparatus 10 includes a communications device 110 which will signal the presence of a welding flaw and identify its location.

Still further, and referring again to FIG. 15, a mode converted wave, (the 77° shear wave as shown in the figure) which has originated from the LOF welding defect may be used to detect the presence of same. FIGS. 16 and 17 show the same technique, except in these examples, the ultrasonic waves are used to inspect various portions of the partially completed welds. For V-groove weld preparations, the reflection off the LOF welding defect can be arranged to follow exactly the reverse path of the incident wave being reflected off the bottom surface. In this situation, the transmitting transducer 66 is also the receiving transducer. Further, the angle of the ultrasonic beam is arranged such that it is perpendicular to the weld side wall 25. This will provide the maximum reflected amplitude in the correct direction where an LOF welding defect is present. This technique was described in significant detail in U.S. Pat. No. 4,712,722, the teachings of which are incorporated herein by reference, therefore further disclosure of the method is not warranted.

The technique described above can be used to detect the upper and lower location where an LOF welding defect begins and ends. In this technique which has been termed the "pulse-echo" ultrasonic method, transmitted sound returns to the transmitting transducer 66 where it is subsequently detected. In this pulse-echo method, the relevant echo travels in the reverse direction along the same path as the incident beam. In the implementation of the method, the transducer 66 is moved generally laterally outwardly relative to the partially completed weld, and a series of echoes will be observed from different areas of the weld. For example, when the beam is centered at the base of a partially completed weld 14, an echo is often observed due to roughness at the root of the weld. This is often viewed as a benign weld deflect. As the transducer 66 moves laterally outwardly relative to the direction of the partially completed weld 14, the ultrasonic beam moves higher on the partially completed weld 14. When the ultrasonic beam reaches the bottom of an LOF weld defect, another echo will be seen. This echo will be earlier in time than the echo from the root. The next echo is observed when the ultrasonic beam reaches the top of the LOF welding defect. This echo may be an echo which will be observed also from the top of the partially completed weld. As described above, the present method provides a means by which an LOF welding defect may be accurately detected and located without relying on specular reflections. Still further, it has been found that the present device 10 has usefulness in detecting the porosity of a partially completed weld. For example, such pulse-echo signals typically have a different character than the reflections from the LOF welding defect and may be discriminated from the LOF welding defect signals by an appropriate signal processing algorithm.

In addition to the foregoing, another type of welding flaw that the present device 10 is operable to detect concerns a welding flaw which is directed to a lack of penetration in the root pass, hereinafter identified as "LOP". LOP in the root pass can be detected by the present method in narrow groove partially completed welds 14 by observing a large reflected energy from the unwelded bevel in the root of the weld preparation. This reflected amplitude is much larger than that reflected from the usual roughness at the root of the weld. Still further, hot cracking can occur under certain conditions often during the root pass of the automated welder 11. This results in a substantially planer crack developing and running generally in the direction of the partially completed weld 14 and approximately in the center thereof. In the case of hot cracking, the earlier described methods may be used to detect this welding flaw since ultrasound will not be transmitted through such a crack.

The aforementioned pitch-catch technique can be combined with a corresponding reflection or pulse-echo method to allow the apparatus of the present invention 10 to confirm the presence and location of a particular welding flaw. For example, and as seen in FIGS. 4, 5, and 6, both the pitch-catch method and the pulse-echo method can be used to find an LOF welding defect by utilizing the arrangement in these figures. The combination of both techniques can significantly improve the probability of detection. For example, and referring now to FIGS. 3, 4 and 5, a transducer 66 positioned on one side of the partially completed weld 14 may be pulsed and simultaneously receive the pulse-echo signal on the same side. Additionally, this same transducer, on one side of the weld, may send an ultrasonic signal and the transducer 60 which is located on the opposite side of the partially completed weld 14 may receive same. The reverse arrangement could also be utilized. As was disclosed earlier, the ultrasonic signal generators and receivers may be selectively moved along the individual paths of travel 60 or may be moved in unison as shown in FIG. 3. By utilizing the pitch-catch technique, earlier disclosed, an ultrasonic signal will be lost in the presence of an LOF welding defect when the transducers 66 are in such a position that the beam passes through the region of the LOF welding defect. Still further, the loss of amplitude that the particular transducer 66 detects in comparison to other transducer positions where the beam subsequently passes through a good weld provides a means for locating the position of the LOF welding defect. In addition, the loss of the ultrasonic signal as the beam reaches the region at the top of the weld material can be used to measure the welding bead height. In the case of the reflection and pulse-echo techniques, scanning of the individual ultrasonic signal generators and receivers 50, and 80 generally laterally outwardly relative to the direction of the partially completed weld allows discrimination between the echo coming from the top of an LOF welding defect and those that may come about as a result of reflections coming from the root and the top of the bead of the welding material.

Figure 18:
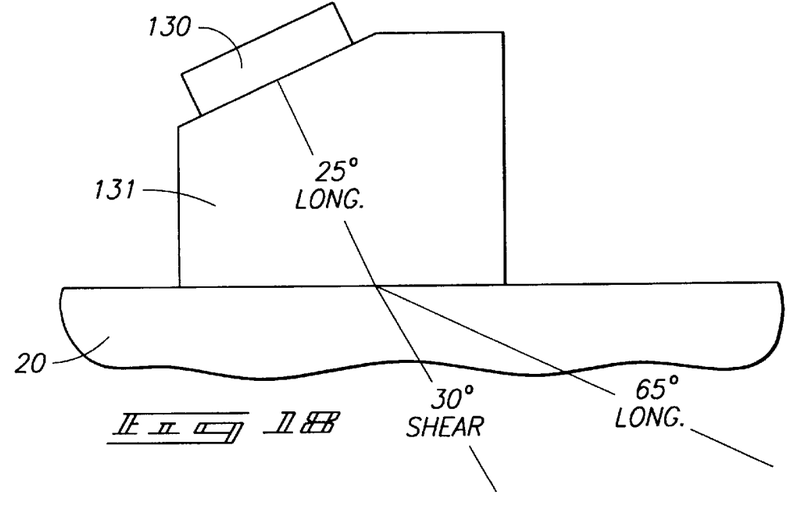
FIG. 18 is a greatly simplified, transverse, vertical sectional view of the ultrasonic beams produced by a wedge mounted piezoelectric transducer.
Figure 19:
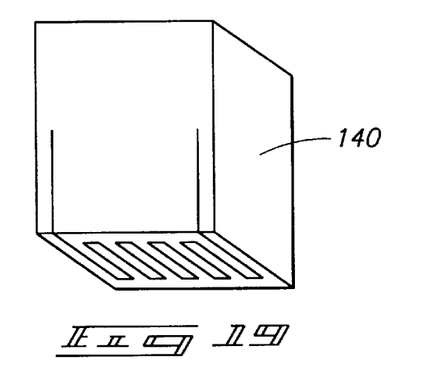
FIG. 19 is a greatly simplified schematic view of a meanderline electromagnetic acoustic transducer.

Referring now to FIGS. 18 and 19, respectively, piezoelectric transducers 130 and electromagnetic acoustic transducers (EMATs) 140 can be configured to implement the inspection techniques described earlier. These particular transducers 66 can be fabricated to generate and receive both shear wave and mode converted waves substantially at the same time. In the case of the piezoelectric transducers 130, given angled ultrasonic beams produced by the piezoelectric transducer are achieved by mounting this same device on a wedge of polymeric material, such as Lucite™ which has been formed at a predetermined angle. This wedge of material 131 as seen in FIG. 18, produces a longitudinal wave in the wedge. This longitudinal ultrasonic wave then travels to the interface between the wedge 131 and the object to be inspected 20. Both the shear and longitudinal ultrasonic waves are transmitted into the given object to be inspected at angles determined by the following formula:

$$\frac{SIN(\theta_{wedge})}{V_{wedge}} = \frac{SIN(\theta_{shear})}{V_{shear}} = \frac{SIN(\theta_{longitudinal})}{V_{longitudinal}}$$

In the formula noted above, the longitudinal wave speed for a material such as Lucite™ is approximately 2.67 millimeters per millisecond. Thus, to produce or detect both 30° shear waves and 65° longitudinal waves, the Lucite wedge is chosen to be approximately 25°. As would be expected, materials other than polymeric compound comprising Lucite™ may be used, and the transducer 66 may be mounted inside a liquid filled tire with the liquid and tire playing essentially the identical role that the Lucite™ material would play, that is, the ultrasound waves being transmitted through the liquid and tire and into the object to be inspected 20.

The beam width of a piezoelectric transducer 130 is determined by the wavelength produced by same and the size of the respective transducer. By selecting an appropriate beam width, the entire partially completed weld can be reviewed by any one of the methods shown above.

Figure 20:
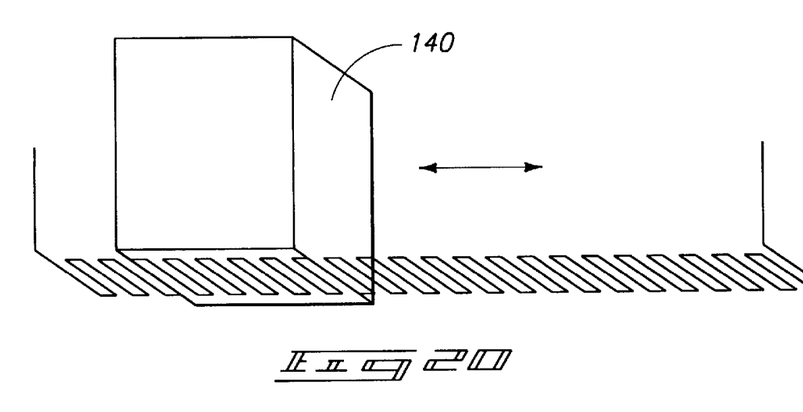
FIG. 20 is a greatly simplified schematic view of an extended meanderline coil with an active area determined by the magnet position.

As seen in FIGS. 19 and 20, an electromagnetic acoustic transducer (EMAT) produced with a meanderline coil produces longitudinal and shear waves which are additionally movable by changing the frequency of the ultrasonic wave.

Still further, the size of the ultrasonic beam emitted for an EMAT may be determined by the size of the active coil and the wavelength of operation. In addition, the frequency band width of the ultrasonic wave also effects the beam size. The construction of an EMAT allows a simple scanning mechanism. For example, the meanderline coil will be positioned next to the object to be inspected 20. Thereafter, a magnet produces a magnetic field in the coil, and into the object to be inspected. The corresponding signal is determined by the position of the magnet. The coil can be of any size. The active area of the coil where the ultrasound signal can be generated or received is determined by the region where the magnetic flux is the highest. Thus, the effective position of the transducer 66 can be adjusted by simply moving the magnet.

Operation

The operation of the described embodiment of the present invention is believed to be readily apparent, and is briefly summarized at this point.

As best seen in FIGS. 1 to 6, an apparatus for the concurrent nondestructive evaluation of partially completed welds 10 is shown. The partially completed welds 14 have opposite sides 26 and 27, and which are used in combination with an automated welder 11. In the preferred embodiment, the apparatus 10 includes an ultrasonic signal generator 50 mounted on the welder 11 and which generates an ultrasonic signal which is directed toward one side of the partially completed weld 14; an ultrasonic signal receiver 80 mounted on the automatic welder 11 for detecting ultrasonic signals which are transmitted by the ultrasonic signal generator 50 and which are reflected or diffracted from one side of the partially completed weld 14 or which passes through a given region of the partially completed weld 14; and an analysis assembly 91 coupled with the ultrasonic signal receiver which processes the ultrasonic signals received by the ultrasonic signal receiver to identify the welding flaws in the partially completed weld.

As seen most clearly by references to FIGS. 5 and 6, second ultrasonic signal generators 50 are provided and mounted on the opposite side of the partially completed weld 14 and generate an ultrasonic signal which is transmitted in the direction of the opposite side of the partially completed weld. The device of the present invention also includes, as seen in FIG. 1, a communications device 110 which is coupled with the analysis assembly 91 and which identifies the location of each welding flaws which exceeds predetermined parameters. These predetermined parameters may include such indicia as size and the type of welding flaw involved. In addition, the communication device 110 may provide machine readable indicia which identifies the location and type of welding flaw.

As described earlier, the ultrasonic signal generators 50 and ultrasonic signal receivers 80 utilized with the present apparatus 10 are positioned laterally outwardly relative to one side of the partially completed weld 14 and can be adjusted during ongoing welding operations to locate the respective generators and receivers in an appropriate position to confirm the location and identity of various welding flaws. As will be seen, the apparatus of the present invention 10 provides a convenient means where several different ultrasonic techniques can be utilized, in combination, to identify, locate and confirm the presence of various welding defects on a concurrent, real time basis. The present device 10 is simple in operation, economical to operate, and provides additional benefits not available with the prior art techniques utilized heretofore to address the same or similar problems.

In addition to the foregoing, the present device 10 comprises a convenient method for the concurrent nondestructive evaluation of partially completed welds. In this regard, the method comprises providing an ultrasonic signal generator 50 and ultrasonic signal receiver 80 which are mounted in trailing relation to the direction of travel of the automated welder; locating the ultrasonic generator 50 and ultrasonic signal receiver 80 in a given position which is substantially laterally outwardly relative to one side of the partially completed weld 14 during welding operations; emitting ultrasonic signals which are directed to a region adjacent to the partially completed weld; detecting the ultrasonic signals which are emitted by the ultrasonic signal generator 50 and which are reflected, diffracted, or passed through the partially completed weld 14 and which are received by the ultrasonic signal receiver 80; and interpreting the ultrasonic signals which are reflected, diffracted or passed through the partially completed weld 14 to identify predetermined welding flaws. The method of the present invention further includes adjustably controlling the positional relationship of the ultrasonic signal generator 50 and ultrasonic signal receiver 80 relative to one side of the partially completed weld 14 during welding operations, and further, controlling the automated welder operations with respect to the type and number of welding flaws identified during the interpreting step.

In compliance with the statute, the invention been described in language more or less specific as to structure and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims, appropriately interpreted in accordance with the Doctrine of Equivalents.

I claim:

1. Apparatus for the concurrent non-destructive evaluation of partially completed welds which have opposite sides and which is used in combination with an automated welder, comprising:

an ultrasonic signal generator mounted on the welder and which generates an ultrasonic signal which is directed toward one side of a partially completed weld, and wherein the automated welder moves along a path of travel and the ultrasonic signal generator is located in spaced trailing relation relative to the automated welder, and further operates concurrently with the operation of the automated welder to evaluate the partially completed weld;

an ultrasonic signal receiver mounted on the welder for detecting ultrasonic signals which are transmitted by the ultrasonic signal generator and which are reflected or diffracted from one side of the partially completed weld or which pass through a given region of the partially completed weld; and an analysis assembly coupled with the ultrasonic signal receiver and which processes the ultrasonic signals received by the ultrasonic signal receiver to confirm the presence and location of welding flaws in the partially completed weld.

2. An apparatus as claimed in claim 1, wherein a second ultrasonic signal generator is mounted on the opposite side of the partially completed weld and generates an ultrasonic signal which is transmitted in the direction of the opposite side of the partially completed weld.

3. An apparatus as claimed in claim 1, wherein a second ultrasonic signal receiver is mounted on the opposite side of the partially completed weld.

4. An apparatus as claimed in claim 1, wherein the analysis assembly comprises a digital computer which distinguishes between a plurality of predetermined welding flaws.

5. An apparatus as claimed in claim 4, and further comprising:

a communication device coupled with the analysis assembly and which identifies the location of each welding flaw which exceeds predetermined parameters.

6. An apparatus as claimed in claim 5, wherein the communication device identifies the size and type of welding flaw.

7. An apparatus as claimed in claim 6, wherein the communication device provides machine readable indicia which identifies the type and location of the welding flaw.

8. An apparatus as claimed in claim 1, and further comprising a control assembly coupled with the automated welder and the analysis assembly and which stops the operation of the automated welder when the number of welding flaws reach a predetermined number or a given size.

9. An apparatus as claimed in claim 1, wherein the ultrasonic signal generator and the ultrasonic signal receiver are positioned on one side of the partially completed weld, and wherein a second ultrasonic generator and ultrasonic signal receiver are positioned on the opposite side of the partially completed weld, and wherein the respective ultrasonic signal receivers receive ultrasonic signals which are emitted by the ultrasonic signal generator which is positioned on the opposite side of the partially completed weld.

10. An apparatus as claimed in claim 1, wherein the ultrasonic signal generator and the ultrasonic signal receiver are positioned on one side of the partially completed weld, and wherein a second ultrasonic generator and ultrasonic signal receiver are positioned on the opposite side of the partially completed weld, and wherein the respective ultrasonic signal receivers receive ultrasonic signals which are emitted by the ultrasonic signal generator which is positioned on the same side of the partially completed weld.

11. An apparatus as claimed in claim 1, wherein the ultrasonic signal generator and the ultrasonic signal receiver are individually positioned on one side of the partially completed weld, and wherein a second ultrasonic generator and ultrasonic signal receiver are positioned on the opposite side of the partially completed weld, and wherein the respective ultrasonic signal receivers receive ultrasonic signals which are emitted by the ultrasonic signal generator which is positioned on both the same side and the opposite side of the partially completed weld.

12. An apparatus as claimed in claim 1, wherein the ultrasonic signal generator and ultrasonic signal receiver are positioned laterally outwardly relative to one side of the partially completed weld, and wherein the position of the ultrasonic signal generator can be adjusted during on-going welding operations.

13. An apparatus as claimed in claim 1, wherein the ultrasonic signal generator and ultrasonic signal receiver are positioned laterally outwardly relative to one side of the partially completed weld, and wherein the position of the ultrasonic signal receiver can be adjusted during on-going welding operations.

14. An apparatus as claimed in claim 1, wherein the ultrasonic signal generator and ultrasonic signal receiver are positioned laterally outwardly relative to one side of the partially completed weld, and wherein the position of both the ultrasonic signal generator and the ultrasonic signal receiver is selectively adjusted during on-going welding operations.

15. An apparatus as claimed in claim 1, wherein the ultrasonic signal generator and the ultrasonic signal receiver are mounted on one side of the partially completed weld, and wherein a second ultrasonic signal generator and ultrasonic signal receiver are positioned on the opposite side of partially completed weld, and wherein the position of each of the ultrasonic signal generators and ultrasonic signal receivers can be adjusted during on-going welding operations.

16. An apparatus as claimed in claim 1, wherein the ultrasonic signal generator and the ultrasonic signal receiver are each mounted on one side of the partially completed weld, and wherein a second ultrasonic signal generator and ultrasonic signal receiver are mounted on the opposite side of the partially completed weld, and wherein the position of each of the ultrasonic signal generators and ultrasonic signal receivers can be adjusted during on-going welding operations, and wherein the ultrasonic signal generator and ultrasonic signal receiver positioned on each side of the partially completed weld move in unison together.

17. An apparatus as claimed in claim 1, wherein the ultrasonic signal generator and ultrasonic signal receiver are individually movably mounted on one side of the partially completed weld, and wherein a second ultrasonic signal generator and ultrasonic signal receiver are individually movably mounted on the opposite side of the partially completed weld, and wherein each ultrasonic signal generator emits an ultrasonic signal which is directed towards one side of the partially completed weld, and wherein the ultrasonic signal emitted by each of the ultrasonic signal generators are reflected, diffracted or passed by the partially completed weld and received by one of the ultrasonic signal receivers, and wherein each of the received ultrasonic signals are correlated by the analysis assembly to confirm the presence and location of a welding flaw.

18. An apparatus as claimed in claim 1, wherein the ultrasonic signal generator and ultrasonic signal receiver comprise a transducer.

19. An apparatus for the concurrent non-destructive evaluation of partially completed welds which have opposite sides, and which is used in combination with an automated welder, comprising:
   an ultrasonic signal generator mounted on and disposed in traveling relation relative to the welder and operable to emit a signal ultrasonic signal, and wherein the ultrasonic signal generator is movably mounted for substantially lateral outward movement relative to one side of the partially completed weld, and wherein the ultrasonic signal generator operates concurrently with the operation of the automated welder to evaluate the partially completed weld;
   an ultrasonic signal receiver borne by the welder and operable to receive the ultrasonic signal emitted by the ultrasonic signal generator, and wherein the ultrasonic signal receiver is movably mounted for substantially lateral outward movement relative to one side of the partially completed weld; and
   an analysis assembly coupled with the ultrasonic signal receiver and which processes the ultrasonic signals received by the ultrasonic signal receiver to identify the welding flaws.

20. An apparatus as claimed in claim 19, wherein the ultrasonic signal generator and ultrasonic signal receiver are located on the same side of the partially completed weld.

21. An apparatus as claimed in claim 19, wherein the ultrasonic signal generator and the ultrasonic signal receiver are individually located on the opposite sides of the partially completed weld.

22. An apparatus as claimed in claim 19, wherein the ultrasonic signal generator and ultrasonic signal receiver are adjustably moveable while the automated welder is in operation.

23. An apparatus as claimed in claim 19, wherein the ultrasonic signal generator and the ultrasonic signal receiver are each movably mounted on the same side of the partially completed weld, and wherein a second ultrasonic signal generator and ultrasonic signal receiver are mounted on the opposite side of the partially completed weld, and wherein each ultrasonic generator emits an ultrasonic signal which is reflected, diffracted or passes through the partially completed weld, and wherein each ultrasonic signal receiver receives one of the ultrasonic signals emitted, and wherein the ultrasonic signals which are received by the respective ultrasonic signal receivers are correlated by the analysis assembly to confirm the presence and location of a welding flaw.

24. An apparatus as claimed in claim 19, and further comprising a communication device coupled with the analysis assembly and which identifies the location, type and size of the welding flaw.

25. An apparatus as claimed in claim 19, wherein the ultrasonic signal generator and ultrasonic signal receiver comprise a transducer.

26. An apparatus for the concurrent non-destructive evaluation of partially completed welds which have opposite sides, and which is used in combination with an automated moveable welder, comprising:
   an ultrasonic signal generator mounted in spaced trailing relation relative to the direction of movement of the automated welder and operable to emit a given ultrasonic signal during operation of the welder in the formation of the partially completed weld, and wherein the ultrasonic signal generator is movably mounted for substantially lateral outward movement relative to one side of the partially completed weld while the automated welder is in operation;
   an ultrasonic signal receiver mounted in spaced trailing relation relative to the direction of movement of the automated welder and operable to receive the ultrasonic signal emitted by the ultrasonic signal generator, and wherein the ultrasonic signal receiver is movably mounted for substantially lateral outward movement relative to the opposite side of the partially completed weld; and
   an analysis assembly coupled with the ultrasonic signal receiver and which processes the ultrasonic signals received by the ultrasonic signal receiver to identify the welding flaws.

27. An apparatus as claimed in claim 26, wherein the ultrasonic signal generator and ultrasonic signal receiver are adjustably moveable while the automated welder is in operation.

28. An apparatus as claimed in claim 26, wherein a second ultrasonic signal generator and ultrasonic signal receiver are each mounted on the opposite sides of the partially completed weld, and wherein each ultrasonic generator emits an ultrasonic signal which is reflected, diffracted or passes through the partially completed weld, and wherein each ultrasonic signal receiver receives one of the ultrasonic signals emitted, and wherein the ultrasonic signals which are received by the respective ultrasonic signal receivers are correlated by the analysis assembly to confirm the presence and location of a welding flaw.

29. An apparatus as claimed in claim 26, and further comprising a communication device coupled with the analysis assembly and which identifies the location, type and size of the welding flaw.

30. An apparatus as claimed in claim 26, wherein the ultrasonic signal generator and ultrasonic signal receiver comprise a transducer.

31. An apparatus for the concurrent non-destructive evaluation of partially completed welds which have opposing sides, and which is used in combination with an automated welder, comprising:
   an ultrasonic signal generator mounted in spaced trailing relation relative to the direction of movement of the automated welder and operable to emit a given ultrasonic signal during the operation of the automated welder in the formation of the partially completed weld, and wherein the ultrasonic signal generator is movably mounted for substantially lateral outward movement relative to one side of the partially completed weld while the automated welder is in operation;
   an ultrasonic signal receiver mounted in spaced trailing relation relative to the direction of movement of the automated welder and operable to receive the ultrasonic signal emitted by the ultrasonic signal generator, and wherein the ultrasonic signal receiver is movably mounted for substantially lateral outward movement relative to the same side of the partially completed weld; and an analysis assembly coupled with the ultrasonic signal receiver and which processes the ultrasonic signals received by the ultrasonic signal receiver to identify the welding flaws.

32. An apparatus as claimed in claim 31, wherein the ultrasonic signal generator and ultrasonic signal receiver are adjustably moveable while the automated welder is in operation.

33. An apparatus as claimed in claim 31, wherein a second ultrasonic signal generator and ultrasonic signal receiver are both mounted on the opposite side of the partially completed weld, and wherein the ultrasonic signals which are received by the respective ultrasonic signal receivers are correlated by the analysis assembly to confirm the presence and location of a welding flaw.

34. An apparatus as claimed in claim 31, and further comprising a communication device coupled with the analysis assembly and which identifies the location, type and size of the welding flaw.

35. An apparatus as claimed in claim 31, wherein the ultrasonic signal generator and ultrasonic signal receiver comprise a transducer.

36. An apparatus for the concurrent non-destructive evaluation of partially completed welds which have opposite sides, and which is used in combination with an automated welder, comprising:

an ultrasonic signal generator mounted in spaced trailing relation relative to the direction of movement of the automated welder and which is operable to emit a given ultrasonic signal, and wherein the ultrasonic signal generator is movably mounted for substantially lateral outward movement relative to one side of the partially completed weld while the automated welder is in operation;

an ultrasonic signal receiver mounted in spaced trailing relation relative to the direction of movement of the automated welder and which is operable to receive the ultrasonic signal emitted by the ultrasonic signal generator, and wherein the ultrasonic signal receiver is movably mounted for substantially lateral outward movement relative to the opposite side of the partially completed weld;

an analysis assembly coupled with the ultrasonic signal receiver and which processes the ultrasonic signals received by the ultrasonic signal receiver to identify the welding flaws;

a communication device coupled with the analysis assembly and which identifies the location, size and type of welding flaw in response to the ultrasonic signal received by the ultrasonic signal receiver; and a control assembly coupled with the automated welder, analysis assembly, ultrasonic signal generator and ultrasonic signal receiver, and wherein the control assembly adjustably positions the ultrasonic signal generator and the ultrasonic signal receiver laterally outwardly relative to the partially completed weld, and wherein the control assembly further stops the operation of the automated welder when the number of welding flaws reach a given number or type.

37. An apparatus as claimed in claim 36, wherein the ultrasonic signal generator and ultrasonic signal receiver comprise a transducer.

38. An apparatus as claimed in claim 36, wherein a second ultrasonic signal generator and ultrasonic signal receiver are both mounted on the opposite side of the partially completed weld, and wherein the ultrasonic signals which are received by the respective ultrasonic signal receivers are correlated by the analysis assembly to confirm the presence and location of a welding flaw.

39. A method for the concurrent, non-destructive evaluation of partially completed welds which have opposite sides, and which is used in combination with an automated moveable welder, comprising:

providing an ultrasonic signal generator and ultrasonic signal receiver which are mounted in trailing relation relative to the direction of travel of the automated welder;

locating the ultrasonic generator and ultrasonic signal receiver in a given position which is substantially laterally outwardly relative to one side of the partially completed weld during welding operations;

emitting ultrasonic signals which are directed to a region adjacent to the partially completed weld while the automated moveable welder is in operation forming the partially completed weld;

detecting the ultrasonic signals which are emitted by the ultrasonic signal generator and which are reflected, diffracted or passed through the partially completed weld and which are received by the ultrasonic receiver; and interpreting the ultrasonic signals which are reflected, diffracted or passed through the partially completed weld to identify predetermined welding flaws.

40. A method as claimed in claim 39, wherein after the step of locating the ultrasonic signal generator and ultrasonic signal receiver, the method further comprises:

adjustably controlling the positional relationship of the ultrasonic signal generator and ultrasonic signal receiver relative to one side of the partially completed weld during welding operations.

41. A method as claimed in claim 39, wherein after the step of interpreting the ultrasonic signals, the method further comprises:

controlling the automated welder operations in response to the type, number, and size of the welding flaws identified during the interpreting step.

* * * * *